US012685712B2

(12) United States Patent
Wu et al.

(10) Patent No.: US 12,685,712 B2
(45) Date of Patent: Jul. 21, 2026

(54) CHITOSAN-Fe COATING-BASED SYNBIOTIC MICROCAPSULE WITH GASTRIC ACID RESISTANCE AND INTESTINAL TARGETED RELEASE AND PREPARATION METHOD THEREOF

(71) Applicant: China Agricultural University, Beijing (CN)

(72) Inventors: Yi Wu, Nanjing City (CN); Ling Guo, Nanjing City (CN); Zeyu Zhang, Nanjing City (CN); Dongli Ma, Nanjing City (CN); Zhiguo Xing, Nanjing City (CN); Liming Xia, Nanjing City (CN)

(73) Assignee: China Agricultural University, Beijing (CN)

( * ) Notice: Subject to any disclaimer, the term of this patent is extended or adjusted under 35 U.S.C. 154(b) by 303 days.

(21) Appl. No.: 18/015,193

(22) PCT Filed: Jul. 23, 2021

(86) PCT No.: PCT/CN2021/108042
§ 371 (c)(1),
(2) Date: Jan. 9, 2023

(87) PCT Pub. No.: WO2022/188335
PCT Pub. Date: Sep. 15, 2022

(65) Prior Publication Data
US 2024/0033226 A1     Feb. 1, 2024

(30) Foreign Application Priority Data
Mar. 10, 2021     (CN) ......................... 202110261530.1

(51) Int. Cl.
*A61K 9/50* (2006.01)
*A61K 35/00* (2006.01)
*A61K 36/02* (2006.01)
*A61K 36/605* (2006.01)
*A61K 36/87* (2006.01)

(52) U.S. Cl.
CPC ............ *A61K 9/5036* (2013.01); *A61K 9/501* (2013.01); *A61K 9/5089* (2013.01); *A61K 36/02* (2013.01); *A61K 36/605* (2013.01); *A61K 36/87* (2013.01); *A61K 2035/115* (2013.01)

(58) Field of Classification Search
CPC ........ A61K 35/744; A61K 35/74; A61K 9/50; A61K 9/5094; A61K 9/5161
See application file for complete search history.

(56) References Cited

FOREIGN PATENT DOCUMENTS

| | | | | | |
|---|---|---|---|---|---|
| CA | 3063623 | A1 * | 11/2018 | ............. | A61P 25/28 |
| CN | 104872677 | A | 9/2015 | | |
| CN | 106387967 | A | 2/2017 | | |
| CN | 108354181 | A | 8/2018 | | |
| CN | 108669565 | A | 10/2018 | | |
| CN | 109527563 | A | 3/2019 | | |
| CN | 112890204 | A | 6/2021 | | |
| CN | 112999198 | A | 6/2021 | | |
| WO | 9747323 | A2 | 12/1997 | | |
| WO | WO 97/47323 | * | 12/1997 | | |
| WO | WO-2015000972 | A1 * | 1/2015 | ............. | A61P 31/04 |
| WO | WO-2015009407 | A1 * | 1/2015 | ............. | A61P 25/00 |
| WO | 2019014222 | A1 | 1/2019 | | |
| WO | 2020219700 | A1 | 10/2020 | | |

OTHER PUBLICATIONS

Rahul et al., Colloids and Surfaces B: Biointerfaces, 2020; 195(111247):1-9 (Year: 2020).*
Naiyuan Cui et al., "Preparation of Pectin/Chitosan Synbiotic Microcapsules and Its Study on Simulated Gastrointestinal Environments and Storage Stability," China Animal Husbandry and Veterinary Medicine, vol. 47, Issue 9, 2020, pp. 2799-2807 (Including English Translation of Abstract).
PCT International Search Report and Written Opinion dated Dec. 15, 2021, PCT International Application No. PCT/CN2021/108042, pp. 1-12 (Including English Translation of ISR).
First Office Action dated Mar. 30, 2022, Chinese Application No. 202110261530.1, pp. 1-8 (Including English Translation).

* cited by examiner

*Primary Examiner* — Brian Gangle
*Assistant Examiner* — Lakia J Jackson-Tongue
(74) *Attorney, Agent, or Firm* — Resolute Legal PLLC

(57)               ABSTRACT
The present disclosure provides a chitosan-Fe coating-based synbiotic microcapsule with gastric acid resistance and intestinal targeted release and a preparation method thereof. The preparation method includes the following steps: preparation of mixed probiotics, preparation of a chitosan-Fe coating, preparation of a microcapsule, and freeze-drying. In the present disclosure, live probiotics wrapped in the microcapsule can avoid a weak acid resistance and a poor long-term storage stability of the probiotics; chitosan-Fe added to a wall material can significantly improve an embedding rate of the microcapsule, and can also achieve targeted release of the probiotics in the intestinal tract.

6 Claims, No Drawings

CHITOSAN-Fe COATING-BASED SYNBIOTIC MICROCAPSULE WITH GASTRIC ACID RESISTANCE AND INTESTINAL TARGETED RELEASE AND PREPARATION METHOD THEREOF

CROSS REFERENCE TO RELATED APPLICATIONS

This application is a National Stage Application of International Application No. PCT/CN2021/108042 filed Jul. 23, 2021, which claims the benefit and priority of Chinese Patent Application No. 202110261530.1, filed with the China National Intellectual Property Administration on Mar. 10, 2021, the disclosures of which are incorporated by reference herein in their entirety as part of the present application.

TECHNICAL FIELD

The present disclosure relates to a synbiotic microcapsule, in particular to a chitosan-Fe coating-based synbiotic microcapsule with gastric acid resistance and intestinal targeted release and a preparation method thereof.

BACKGROUND

Probiotics are microorganisms that play an important role in regulating and improving the intestinal microecological balance of the host. Probiotics are generally inactivated in large quantities due to high-intensity production and processing. Conventional addition cannot protect the probiotics from gastric acid, bile salts, and digestive enzymes. As a result, it is difficult for a sufficient number of viable bacteria to reach the intestinal tract and settle on the intestinal mucosa to exert physiological functions. Embedding is an effective way to increase the activity of probiotics. The studies have found that microcapsule embedding technology is one of the best methods, becoming a hot research topic at home and abroad.

The traditional microcapsule embedding technology has the following problems:

(1) During the preparation, treatments may inactivate the probiotics, such as organic solvents, strong acids or bases, surfactants, excessive heating, mechanical stirring, and aeration.

(2) Some colloidal delivery systems encapsulating small molecules can hardly accommodate probiotics due to an extremely small particle size, resulting in the probiotics being decomposed in the stomach. Moreover, many colloids previously used to encapsulate probiotics do not adequately protect the probiotics during food storage and passage through the intestinal tract.

(3) Many laboratory R&D materials have a high cost, difficult processing, or ingredients that are not suitable for the food industry, making it difficult to achieve commercial applications.

In view of this, it is necessary to develop and improve the microcapsule embedding technology.

SUMMARY

In order to solve the deficiencies of the prior art, an objective of the present disclosure is to provide a chitosan-Fe coating-based synbiotic microcapsule and a preparation method thereof. The microcapsule has a gastric acid resistance and an intestinal targeted release function.

To achieve the above objective, the present disclosure adopts the following technical solutions.

The present disclosure provides a chitosan-Fe coating-based synbiotic microcapsule with gastric acid resistance and intestinal targeted release, prepared by wrapping a core material with a wall material, where the wall material is a mixed solution of a chitosan-Fe solution and a freeze-drying protective agent; and the core material is prepared by mixing 65 parts to 85 parts by weight of a mixed probiotic microbial inoculant, 10 parts to 15 parts by weight of prebiotics, 1 part to 5 parts by weight of pectin, and 5 parts to 10 parts by weight of glycerin.

Preferably, the mixed probiotic microbial inoculant is prepared from one or more selected from the group consisting of *Lactobacillus casei*, *Enterococcus faecalis*, *Enterococcus faecium*, and *Lactobacillus acidophilus*.

More preferably, the prebiotics is one or more selected from the group consisting of mulberry polysaccharides, seaweed polysaccharides, and a grape seed extract.

Furthermore preferably, the synbiotic microcapsule is selected from the group consisting of a chitosan-Fe coating-based mixed microcapsule of the *Lactobacillus casei* and the *Enterococcus faecalis*, a chitosan-Fe coating-based mixed microcapsule of the *Lactobacillus casei* and the *Lactobacillus acidophilus*, and a chitosan-Fe coating-based mixed microcapsule of the *Enterococcus faecium* and the *Lactobacillus acidophilus*.

The present disclosure further provides a preparation method of a chitosan-Fe coating-based synbiotic microcapsule with gastric acid resistance and intestinal targeted release, including the following steps:

S1, preparation of mixed probiotics: conducting culture on a probiotic microbial inoculant to a late logarithmic growth phase, collecting cells, washing the cells several times with a sterile physiological saline to remove a medium, suspending washed cells in the sterile physiological saline, and adjusting a concentration of the cells to $1*10^8$ CFU/mL for later use;

S2, preparation of a chitosan-Fe coating: adding 1 g to 5 g of chitosan to 100 mL to 500 mL of a sodium citrate buffer with a pH value of 4.0 to 5.5, adding 6 mg to 10 mg of $FeSO_4 \cdot (H_2O)_x$, stirring at a room temperature for 1 h to 6 h, and conducting sterilization for later use;

S3, preparation of a microcapsule: mixing 65 parts to 85 parts by weight of a mixed probiotic microbial inoculant, 10 parts to 15 parts by weight of prebiotics, 1 part to 5 parts by weight of pectin, and 5 parts to 10 parts by weight of glycerin obtained in step S1 uniformly to obtain a core material; extruding the core material into a sterilized $CaCl_2$ solution by an extrusion method and soaking for 30 min to 60 min, adding a soaked core material into a chitosan-Fe coating solution prepared in step S2 to conduct constant-temperature magnetic stirring for 1 h to 3 h, and washing and filtering to obtain the microcapsule; and S4, freeze-drying: freeze-drying the microcapsule obtained in step S3 to obtain the synbiotic microcapsule.

Preferably, in step S1, the probiotic microbial inoculant includes one or more of *Lactobacillus casei*, *Enterococcus faecalis*, *Enterococcus faecium*, and *Lactobacillus acidophilus*.

More preferably, in step S2, the sterilization is conducted at 121° C. for 30 min.

Further preferably, in step S3, the $CaCl_2$) solution has a molar concentration of 0.3 M.

Furthermore preferably, in step S4, the freeze-drying specifically includes: adding the microcapsule obtained in step S3 to a glycerin solution with a volume fraction of 10% to 15%, conducting equilibration for 30 min to 60 min, pre-freezing in a −20° C. to −80° C. refrigerator for 2 h to 5 h, and freeze-drying in vacuum at −40° C. to −80° C. for 24 h to 72 h to obtain the synbiotic microcapsule.

Furthermore preferably, in step S4, the freeze-drying specifically includes: adding the microcapsule obtained in step S3 to the glycerin solution with a volume fraction of 10% to 15%, conducting equilibration for 30 min, pre-freezing in a −25.0° C. refrigerator for 5 h, and freeze-drying in vacuum at −80.0° C. for 24 h to 72 h to obtain the synbiotic microcapsule.

The present disclosure has the following beneficial effects:

(1) In the present disclosure, live probiotics wrapped in the microcapsule can avoid a weak acid resistance and a poor long-term storage stability of the probiotics.

(2) Through vacuum freeze-drying, the water content of probiotics is reduced, and the loss of enzyme activity is avoided; moreover, the freeze-dried bacterial powder has desirable rehydration, thorough dehydration, long shelf life, and convenient storage, transportation, and use. During the freeze-drying, an extremely low temperature may lead to damage or even death of bacterial cells, adversely affecting the production and preservation of bacteria. Accordingly, the freeze-drying protective agent (glycerin and pectin) can protect the bacteria from exposure to low temperature to a certain extent during the production of probiotic preparations.

(3) In the present disclosure, in the synbiotic microcapsule obtained by the preparation method, the chitosan-Fe added in the wall material can significantly improve an embedding rate of the microcapsule, indicating that the coating is a protective agent for the probiotics, showing a better encapsulation effect for probiotics.

(4) Since $Fe^{3+}$ has an affinity for amino groups, a gel can be formed under a strong force, thereby effectively preventing the microcapsule from damages of gastric acid; meanwhile, when the gel reaches the intestinal tract, ferric hydroxide is formed due to changes of the pH value, such that the gel is ruptured by reactions to achieve targeted release of probiotics in the intestinal tract.

DETAILED DESCRIPTION OF THE EMBODIMENTS

The present disclosure will be described in detail below in conjunction with specific examples.

In the present disclosure, all raw materials used are commercially available, unless otherwise specified.

Example 1: Preparation of Chitosan-Fe Coating-Based Mixed Microcapsule of *Lactobacillus casei* and *Enterococcus faecalis*

In this example, a preparation method of the synbiotic microcapsule included the following steps:

S1, preparation of mixed probiotics:

A *Lactobacillus casei* seed solution was inoculated into an MRS medium at an inoculum size of 1%, and cultured anaerobically at 37° C. for 24 h, and a bacterial slurry was collected by centrifugation; after washing twice with a sterile physiological saline at a mass concentration of 0.9%, the bacterial slurry was suspended in the 0.9% sterile physiological saline to obtain a *Lactobacillus casei* bacterial suspension.

An *Enterococcus faecalis* seed solution was inoculated into an MRS medium at an inoculum size of 1%, and cultured anaerobically at 37° C. for 24 h, and a bacterial slurry was collected by centrifugation; after washing twice with a 0.9% sterile physiological saline, the bacterial slurry was suspended in the 0.9% sterile physiological saline to obtain an *Enterococcus faecalis* bacterial suspension.

The *Lactobacillus casei* bacterial suspension and the *Enterococcus faecalis* bacterial suspension of an equal concentration were mixed in a mass ratio of 1:1 to obtain the mixed probiotics.

S2, preparation of a chitosan-Fe coating: 1 g of chitosan was added to 200 mL of a sodium citrate buffer with a pH value of 4.6, 6 mg of $FeSO_4 \cdot (H_2O)_x$ was added, stirred at a room temperature for 2 h, and sterilization was conducted at 121° C. for 30 min for later use.

S3, preparation of a microcapsule: 10 g of glycerin was dissolved in 100 mL of water, added with 4 g of pectin, and mixed well. An obtained mixture, the mixed probiotic microbial inoculant, and a grape seed extract were uniformly mixed at a mass ratio of 10:10:1 to obtain a core material. The core material was extruded into a sterilized 0.3 M $CaCl_2$) solution by an extrusion method and soaked for 30 min, a soaked core material was added into the chitosan-Fe coating solution prepared in step S3 to conduct magnetic stirring for 2 h, and washed and filtered to obtain the microcapsule.

S4, freeze-drying: the microcapsule obtained in step S3 was added to the glycerin solution with a volume fraction of 10%, equilibration was conducted for 30 min, pre-frozen in a −25.0° C. refrigerator for 5 h, and freeze-dried in vacuum at −80.0° C. for 36 h to obtain the synbiotic microcapsule, namely the chitosan-Fe coating-based mixed microcapsule of *Lactobacillus casei* and *Enterococcus faecalis*.

Comparative Example 1

In this comparative example, a preparation method was provided for uncoated mixed microcapsule of *Lactobacillus casei* and *Enterococcus faecalis*; correspondingly, there was no preparation of a chitosan-Fe coating and embedding, other preparation processes were similar to those in Example 1, as follows:

(1) Preparation of Mixed Probiotics:

A *Lactobacillus casei* seed solution was inoculated into an MRS medium at an inoculum size of 1%, and cultured anaerobically at 37° C. for 24 h, and a bacterial slurry was collected by centrifugation; after washing twice with a 0.9% sterile physiological saline, the bacterial slurry was suspended in the 0.9% sterile physiological saline to obtain a *Lactobacillus casei* bacterial suspension.

An *Enterococcus faecalis* seed solution was inoculated into an MRS medium at an inoculum size of 1%, and cultured anaerobically at 37° C. for 24 h, and a bacterial slurry was collected by centrifugation; after washing twice with a 0.9% sterile physiological saline, the bacterial slurry was suspended in the 0.9% sterile physiological saline to obtain an *Enterococcus faecalis* bacterial suspension.

The *Lactobacillus casei* bacterial suspension and the *Enterococcus faecalis* bacterial suspension of an equal concentration were mixed in a ratio of 1:1 to obtain the mixed probiotics.

(2) preparation of a probiotics microcapsule: 10 g of glycerin was dissolved in 100 mL of water, added with 4 g of pectin, and mixed well. An obtained mixture and the mixed probiotic microbial inoculant were uniformly mixed at a mass ratio of 1:1 to obtain a core material. The core material was extruded into a sterilized 0.3 M $CaCl_2$) solution by an extrusion method and soaked for 30 min, and washed and filtered to obtain the wet microcapsule.

(3) Freeze-Drying

The microcapsule obtained in step (3) was added to the glycerin solution with a volume fraction of 10%, equilibration was conducted for 30 min, pre-frozen in a –25.0° C. refrigerator for 5 h, and freeze-dried in vacuum at –80.0° C. for 36 h to obtain the synbiotic microcapsule.

Example 2: Preparation of Chitosan-Fe Coating-Based Mixed Microcapsule of *Lactobacillus casei* and *Lactobacillus acidophilus*

In this example, a preparation method of the synbiotic microcapsule included the following steps:

S1, preparation of mixed probiotics:

A *Lactobacillus casei* seed solution was inoculated into an MRS medium at an inoculum size of 1%, and cultured anaerobically at 37° C. for 24 h, and a bacterial slurry was collected by centrifugation; after washing twice with a sterile physiological saline at a mass concentration of 0.9%, the bacterial slurry was suspended in the 0.9% sterile physiological saline to obtain a *Lactobacillus casei* bacterial suspension.

A *Lactobacillus acidophilus* seed solution was inoculated into an MRS medium at an inoculum size of 1%, and cultured anaerobically at 37° C. for 24 h, and a bacterial slurry was collected by centrifugation; after washing twice with a 0.9% sterile physiological saline, the bacterial slurry was suspended in the 0.9% sterile physiological saline to obtain a *Lactobacillus acidophilus* bacterial suspension.

The *Lactobacillus casei* bacterial suspension and the *Lactobacillus acidophilus* bacterial suspension of an equal concentration were mixed in a mass ratio of 1:1 to obtain the mixed probiotics.

S2, preparation of a chitosan-Fe coating: 1 g of chitosan was added to 200 mL of a sodium citrate buffer with a pH value of 4.6, 6 mg of $FeSO_4 \cdot (H_2O)_x$ was added, stirred at a room temperature for 2 h, and sterilization was conducted at 121° C. for 30 min for later use.

S3, preparation of a microcapsule: 10 g of glycerin was dissolved in 100 mL of water, added with 4 g of pectin, and mixed well. An obtained mixture, the mixed probiotic microbial inoculant, and a grape seed extract were uniformly mixed at a mass ratio of 10:10:1 to obtain a core material. The core material was extruded into a sterilized 0.3 M $CaCl_2$) solution by an extrusion method and soaked for 30 min, a soaked core material was added into the chitosan-Fe coating solution prepared in step S3 to conduct magnetic stirring for 2 h, and washed and filtered to obtain the microcapsule.

S4, freeze-drying: the microcapsule obtained in step S3 was added to the glycerin solution with a volume fraction of 10%, equilibration was conducted for 30 min, pre-frozen in a –25.0° C. refrigerator for 5 h, and freeze-dried in vacuum at –80.0° C. for 36 h to obtain the synbiotic microcapsule, namely the chitosan-Fe coating-based mixed microcapsule of *Lactobacillus casei* and *Lactobacillus acidophilus*.

Comparative Example 2

In this comparative example, a preparation method was provided for uncoated mixed microcapsule of *Lactobacillus*

*casei* and *Lactobacillus acidophilus*; correspondingly, there was no preparation of a chitosan-Fe coating and embedding, and a specific preparation process was the same as that of Comparative Example 1, except that the raw materials of probiotics were slightly different from those of Comparative Example 1, which were not repeated here.

Example 3: Preparation of Chitosan-Fe Coating-Based Mixed Microcapsule of *Enterococcus faecium* and *Lactobacillus acidophilus*

In this example, a preparation method of the synbiotic microcapsule included the following steps:

S1, preparation of mixed probiotics:

An *Enterococcus faecium* seed solution was inoculated into an MRS medium at an inoculum size of 1%, and cultured anaerobically at 37° C. for 24 h, and a bacterial slurry was collected by centrifugation; after washing twice with a 0.9% sterile physiological saline, the bacterial slurry was suspended in the 0.9% sterile physiological saline to obtain an *Enterococcus faecium* bacterial suspension.

A *Lactobacillus acidophilus* seed solution was inoculated into an MRS medium at an inoculum size of 1%, and cultured anaerobically at 37° C. for 24 h, and a bacterial slurry was collected by centrifugation; after washing twice with a 0.9% sterile physiological saline, the bacterial slurry was suspended in the 0.9% sterile physiological saline to obtain a *Lactobacillus acidophilus* bacterial suspension.

The *Enterococcus faecium* bacterial suspension and the *Lactobacillus acidophilus* bacterial suspension of an equal concentration were mixed in a mass ratio of 1:1 to obtain the mixed probiotics.

S2, preparation of a chitosan-Fe coating: 1 g of chitosan was added to 200 mL of a sodium citrate buffer with a pH value of 4.6, 6 mg of $FeSO_4 \cdot (H_2O)_x$ was added, stirred at a room temperature for 2 h, and sterilization was conducted at 121° C. for 30 min for later use.

S3, preparation of a microcapsule: 10 g of glycerin was dissolved in 100 mL of water, added with 4 g of pectin, and mixed well. An obtained mixture, the mixed probiotic microbial inoculant, and a grape seed extract were uniformly mixed at a mass ratio of 10:10:1 to obtain a core material. The core material was extruded into a sterilized 0.3 M $CaCl_2$) solution by an extrusion method and soaked for 30 min, a soaked core material was added into the chitosan-Fe coating solution prepared in step S3 to conduct magnetic stirring for 2 h, and washed and filtered to obtain the microcapsule.

S4, freeze-drying: the microcapsule obtained in step S3 was added to the glycerin solution with a volume fraction of 10%, equilibration was conducted for 30 min, pre-frozen in a –25.0° C. refrigerator for 5 h, and freeze-dried in vacuum at –80.0° C. for 36 h to obtain the synbiotic microcapsule, namely the chitosan-Fe coating-based mixed microcapsule of *Enterococcus faecium* and *Lactobacillus acidophilus*.

Comparative Example 3

In this comparative example, a preparation method was provided for uncoated mixed microcapsule of *Enterococcus faecium* and *Lactobacillus acidophilus*; correspondingly, there was no preparation of a chitosan-Fe coating and embedding, and a specific preparation process was the same as that of Comparative Example 1, except that the raw materials of probiotics were slightly different from those of Comparative Example 1, which were not repeated here.

Performance Test

The microcapsule embedding rate determination and the in vitro simulation experiment test were conducted on the products prepared by each example and comparative example of the present disclosure. The detection methods and results were as follows:

(1) Determination of Microcapsule Embedding Rate 1 g of a freeze-dried microcapsule product was added to 9 mL of a PBS (pH=7.4), shaken in a shaker at 37° C. and 150 r/min for 1 h, and samples were collected to count viable bacteria.

A calculation formula of the embedding rate was as follows: embedding rate (%)=(the number of viable bacteria in the microcapsule/the number of initial viable bacteria)× 100%.

The determination results of the microcapsule embedding rate were shown in Table 1.

tract. The reason is that: when the chitosan-Fe coating was added, since $Fe^{3+}$ has an affinity for amino groups, a gel can be formed under a strong force, thereby preventing the microcapsule from damages of gastric acid; meanwhile, when the gel reaches the intestinal tract, ferric hydroxide is formed due to changes of the pH value, such that the gel is ruptured by reactions to achieve targeted release of probiotics in the intestinal tract.

The above shows and describes the basic principles, main features, and advantages of the present disclosure. Those skilled in the art should understand that the above examples are not intended to limit the present disclosure in any form, and that any technical solutions obtained by means of equivalent replacement or equivalent transformation should fall within the protection scope of the present disclosure.

TABLE 1

Comparison of embedding rates of synbiotic microcapsules

| Type | Groups | The number of viable bacteria in the microcapsule (CFU/g) | The number of initial viable bacteria (CFU/g) | Embedding rate (%) |
|---|---|---|---|---|
| Chitosan-Fe coating-based synbiotic microcapsule | Example 1 | $5.5*10^7$ | $1.0*10^8$ | 55% |
| | Example 2 | $7.0*10^7$ | $1.0*10^8$ | 70% |
| | Example 3 | $6.0*10^7$ | $1.0*10^8$ | 60% |
| Uncoated synbiotic microcapsule | Comparative Example 1 | $3.0*10^7$ | $1.0*10^8$ | 30% |
| | Comparative Example 2 | $3.8*10^7$ | $1.0*10^8$ | 38% |
| | Comparative Example 3 | $3.5*10^7$ | $1.0*10^8$ | 35% |

As shown in Table 1, in the synbiotic microcapsule obtained by the preparation method, the chitosan-Fe added in the wall material can significantly improve an embedding rate of the microcapsule, indicating that the coating is a protective agent for the probiotics, showing a better encapsulation effect for probiotics.

(2) In Vitro Simulation Experiment Test 1 g of the microcapsule of the present disclosure (the amount of freeze-dried microcapsule added was 0.1 g) was dispersed in 9 mL of an artificially-simulated gastric juice, and shaken in a shaker at 37° C. and 150 r/min; after 90 min, the microcapsule was transferred to 9 mL of a prepared artificial intestinal juice, and shaken in a shaker at 37° C. and 150 r/min; after 90 min, 1 mL of the microcapsule was pipetted for gradient dilution, and viable bacteria were counted using an MRS agar medium. The test results were shown in Table 2.

What is claimed is:

1. A preparation method of a chitosan-Fe coating-based synbiotic microcapsule with gastric acid resistance and intestinal targeted release, comprising the following steps:

S1, preparation of a mixed probiotic microbial inoculant: conducting culture on a probiotic microbial inoculant to a late logarithmic growth phase, collecting cells, washing the cells several times with a sterile physiological saline to remove a medium, suspending washed cells in the sterile physiological saline, and adjusting a concentration of the cells to $1*10^8$ CFU/mL for later use;

S2, preparation of a chitosan-Fe coating solution: adding 1 g to 5 g of chitosan to 100 mL to 500 mL of a sodium citrate buffer with a pH value of 4.0 to 5.5, adding 6 mg to 10 mg of $FeSO_4$:$(H_2O)_x$, stirring at a room temperature for 1 h to 6 h, and conducting sterilization for later use;

TABLE 2

Comparison of colony counts before and after in vitro simulation of microcapsule

| Type | Groups | Colony count (CFU/g) before simulation in vitro | Colony count (CFU/g) after simulation in vitro CFU/g | Embedding rate (%) |
|---|---|---|---|---|
| Chitosan-Fe coating-based synbiotic microcapsule | Example 1 | $5.5*10^7$ | $3.8*10^8$ | 69.10% |
| | Example 2 | $7.0*10^7$ | $4.5*10^8$ | 64.28% |
| | Example 3 | $6.0*10^7$ | $4.0*10^8$ | 66.67% |
| Uncoated synbiotic microcapsule | Comparative Example 1 | $3.0*10^7$ | $8.0*10^8$ | 26.67% |
| | Comparative Example 2 | $3.8*10^7$ | $8.5*10^8$ | 22.37% |
| | Comparative Example 3 | $3.5*10^7$ | $6.8*10^8$ | 19.43% |

As shown in Table 2, the in vitro simulation experiments showed that the chitosan-Fe coating could improve the tolerance of probiotics to gastric acid and the like, such that the probiotics achieved targeted release in the intestinal S3, preparation of a microcapsule: mixing 65 parts to 85 parts by weight of the mixed probiotic microbial inoculant obtained in step S1, 10 parts to 15 parts by weight of prebiotics, 1 part to 5 parts by weight of pectin, and 5 parts to 10 parts by weight of glycerin to obtain a core material; extruding the core material into a sterilized $CaCl_2$ solution by an extrusion method and soaking for 30 min to 60 min, adding a soaked core material into the chitosan-Fe coating solution prepared in step S2 to conduct constant-temperature magnetic stirring for 1 h to 3 h, and washing and filtering to obtain the microcapsule; and S4, freeze-drying: freeze-drying the microcapsule obtained in step S3 to obtain the synbiotic microcapsule.

2. The preparation method of a chitosan-Fe coating-based synbiotic microcapsule with gastric acid resistance and intestinal targeted release according to claim 1, wherein in step S1, the probiotic microbial inoculant comprises one or more of *Lactobacillus casei, Enterococcus faecalis, Enterococcus faecium*, and *Lactobacillus acidophilus*.

3. The preparation method of a chitosan-Fe coating-based synbiotic microcapsule with gastric acid resistance and intestinal targeted release according to claim 1, wherein in step S2, the sterilization is conducted at 121° C. for 30 min.

4. The preparation method of a chitosan-Fe coating-based synbiotic microcapsule with gastric acid resistance and intestinal targeted release according to claim 1, wherein in step S3, the $CaCl_2$) solution has a molar concentration of 0.3 M.

5. The preparation method of a chitosan-Fe coating-based synbiotic microcapsule with gastric acid resistance and intestinal targeted release according to claim 1, wherein in step S4, the freeze-drying specifically comprises: adding the microcapsule obtained in step S3 to a glycerin solution with a volume fraction of 10% to 15%, conducting equilibration for 30 min to 60 min, pre-freezing in a −20° C. to −80° C. refrigerator for 2 h to 5 h, and freeze-drying in vacuum at −40° C. to −80° C. for 24 h to 72 h to obtain the synbiotic microcapsule.

6. The preparation method of a chitosan-Fe coating-based synbiotic microcapsule with gastric acid resistance and intestinal targeted release according to claim 5, wherein in step S4, the freeze-drying specifically comprises: adding the microcapsule obtained in step S3 to the glycerin solution with a volume fraction of 10% to 15%, conducting equilibration for 30 min, pre-freezing in a −25.0° C. refrigerator for 5 h, and freeze-drying in vacuum at −80.0° C. for 24 h to 72 h to obtain the synbiotic microcapsule.

* * * * *